(12) United States Patent  
Leonard et al.

(10) Patent No.: US 8,512,315 B2
(45) Date of Patent: Aug. 20, 2013

(54) SURGICAL DEVICE

(75) Inventors: Robert F. Leonard, Atlanta, GA (US); Michael Merves, Dunwoody, GA (US)

(73) Assignee: CareFusion 2200, Inc., San Diego, CA (US)

(*) Notice: Subject to any disclaimer, the term of this patent is extended or adjusted under 35 U.S.C. 154(b) by 1825 days.

(21) Appl. No.: 11/810,501

(22) Filed: Jun. 6, 2007

(65) Prior Publication Data

US 2008/0306342 A1 Dec. 11, 2008

(51) Int. Cl.
*A61B 17/2909* (2006.01)

(52) U.S. Cl.
USPC .............................................. 606/1; 606/41

(58) Field of Classification Search
USPC ....................... 606/1, 41–52; 607/88–102
See application file for complete search history.

(56) References Cited

U.S. PATENT DOCUMENTS

| 5,489,290 A | 2/1996 | Furnish |
| 5,665,105 A | 9/1997 | Furnish et al. |
| 5,827,323 A | 10/1998 | Klieman et al. |
| 5,922,007 A | 7/1999 | Hoogeboom et al. |

FOREIGN PATENT DOCUMENTS

| DE | 20 2006 005 632 U1 | 6/2006 |
| EP | 1 348 381 A | 10/2003 |
| WO | WO 94/27510 | 12/1994 |

OTHER PUBLICATIONS

International Search Report and Written Opinion for PCT/US2008/065917 dated Feb. 10, 2008.

*Primary Examiner* — Aaron Roane
(74) *Attorney, Agent, or Firm* — Brinks Hofer Gilson & Lione

(57) ABSTRACT

An in-line laparoscopic surgical instrument is provided, including a ratchet mechanism. The ratchet mechanism includes a single actuating means that may be used to engage, release, or defeat a ratchet engagement between portions of the handle.

2 Claims, 16 Drawing Sheets

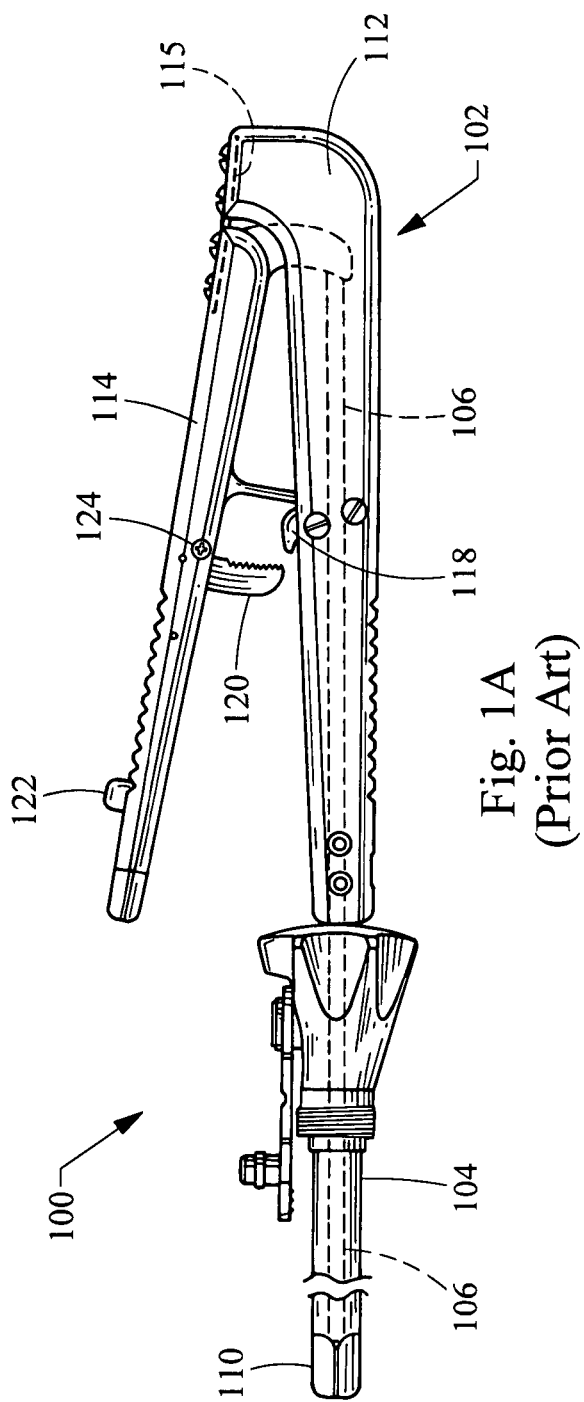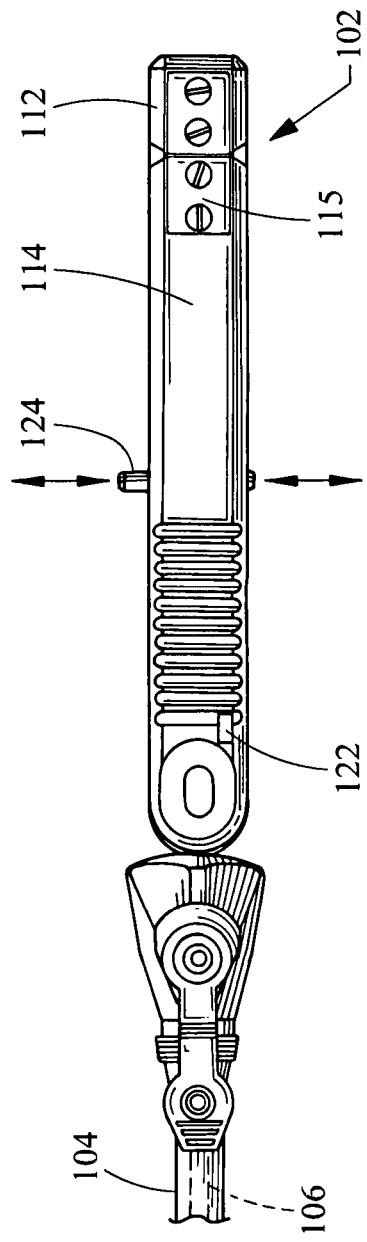
Fig. 1A (Prior Art)
Fig. 1B (Prior Art)

SURGICAL DEVICE

This application claims the benefit of U.S. patent application Ser. No. 11/186,627, filed Jul. 21, 2005, now abandoned, which claims priority to U.S. Provisional Patent Application No. 60/590,095, filed Jul. 21, 2004, each of which is hereby incorporated by reference in its entirety.

FIELD OF THE INVENTION

The present invention relates generally to medical devices, and more particularly to a handle configured to manipulate a distal tool end of a generally axial laparoscopic device.

BACKGROUND

As depicted in FIGS. 1A-1B, a typical axial/in-line laparoscopic tool device 100 generally has five main components: a handle 102, an outer shaft 104 extending longitudinally from the handle, an actuation rod 106 extending through the outer shaft, and an actuatable end effector 110, disposed at the distal end of the device. The handle 102 illustrated is an "in-line handle", which has a stationary handle portion 112 attached to the outer shaft 104 and an actuatable handle portion 114 attached to the actuation rod 106. Actuation of the actuatable handle portion 114 by pivoting relative to the stationary handle portion 112 moves the actuation rod 106 axially within the outer shaft 104 to operate the end effector 110. The actuatable handle portion 114 typically is biased into an open position by a spring such as a hinge spring 115. Some existing devices include a ratchet mechanism to hold the handle portions 112, 114 in a selected position relative to each other. As shown in FIGS. 1A-1B, a known ratchet has a pawl arm 118 that engages a ratchet-toothed arm 120. The ratchet is biased into a disengaged position, but it can be selectably engaged/disengaged by actuating and holding in place a ratchet lever 122 or it can be lockedly disengaged by actuating a separate, transversely mounted, ratchet-locking button 124 that holds the ratchet-toothed element 120 at an angle configured to remain disengaged from the pawl element 118. With this configuration, a user may be required to use his/her opposite hand and/or to change grip position on the handle 102 to reach and actuate the ratchet-locking button 124.

Although different variations of each of the above components have been introduced into the art, there exists a need for designs that provide efficiency in manufacturing, and that provide surgeons and other users with ergonomic features to enhance safety and ease of use. In particular, there is a need for a handle design that includes an easy-to-use locking feature having a minimal number of components to provide for ease of assembly and durability. In particular, there is a need for a durable handle design including a ratchet mechanism that can easily be operated by the user's gripping hand from a variety of grip positions, without requiring a user to significantly alter his/her grip, or to use his/her other hand to engage, disengage, and lock the mechanism.

BRIEF SUMMARY

Embodiments of the present invention may be configured to address the needs in the art for ergonomic designs that present advantages in use and manufacture. Preferred embodiments of the present invention will be configured such that they may be sterilized and reused. In one aspect, embodiments of the present invention may include a ratchet mechanism that is biased such that it engages the handle members with each other when the ratchet mechanism is in a default/rest position. A preferred ratchet mechanism may be configured such that it can be actuated (i.e., engaged, released, or defeated) using a single button, lever, slide, switch, or other actuation means that is positioned conveniently for a user such that the user's grip not be changed significantly for ratchet actuation. This provides an advantage over the prior art ratchet mechanisms that require actuation of two or more separate components and/or that require a user to significantly alter his/her grip—or even require use of another hand (of the user or an assistant)—to actuate a ratchet mechanism between engaged, released, and defeated states. Although embodiments of the present invention are directed to aspects of the handle for a laparoscopic surgical device, those of skill in the art will appreciate that handle embodiments of the present invention may be used with different shaft configurations and end effectors (e.g., needle holders, clamps, scissors, dissectors, graspers), and that such uses are within the scope of the present invention.

In one aspect, the present invention includes an in-line surgical instrument having a handle operatively connected to an elongate shaft, the handle comprising: a first handle member pivotably connected to a second handle member, said pivotable connection being located near a proximal end of both handle members; a first engagement member fixed in and projecting from the first handle member toward the second handle member, a first end portion of the first engagement member being biased into engagement with the second engagement member; and a camming switch pivotably connected to the first handle member and in mechanical communication by an operative contact with the first engagement member; wherein, when the camming switch is disposed at a first angle relative to the first engagement member, the operative contact provided is sufficient to pivot the first engagement member so as to disengagingly overcome the biased engagement of the first engagement member with the second engagement member; and wherein, when the camming switch is at a second angle relative to the first engagement member, the operative contact is sufficient to pivot the first engagement member so as to overcome the biased engagement of the first engagement member with the second engagement member and is sufficient to bias the first engagement member out of engagement with the second engagement member.

In another aspect, the present invention includes an in-line surgical instrument having a handle operatively connected to an elongate shaft, the handle comprising: a first handle member; a second handle member pivotably connected to the first handle member near a proximal end of both handle members; and a ratchet mechanism disposed distal relative to the pivotable connection and configured for removably engaging the first and second handle members, the ratchet mechanism comprising first and second ratchet mechanism portions; wherein the first ratchet mechanism portion comprises: an L-shaped ratchet-toothed engagement member; a cammed lever member; and a camming switch; wherein the L-shaped ratchet-toothed engagement member is mounted pivotably to and projects from the first handle member toward the second handle member, the L-shaped ratchet-toothed engagement member comprising a toothed portion generally perpendicular to a lever-arm projection portion; wherein the camming switch is mounted pivotably to and projects from the first handle member away from the second handle member; wherein the cammed lever member comprises a camming end, a levering end, a pivot axis therebetween connecting the cammed lever member pivotably to the first handle member; and wherein the camming switch contacts the camming end of the cammed lever member and the levering end of the cammed lever member contacts the lever-arm projection of the L-shaped ratchet-toothed engagement member; the camming end comprising a protruding camming surface and a depressed camming surface; and wherein the second ratchet mechanism portion comprises: a pawl member mounted to the second handle member, the pawl member including a pawl tooth portion and a pawl leg portion, wherein the pawl tooth portion projects toward, and is configured to engage with, the toothed portion of the ratchet-toothed engagement member; and wherein, a biasing spring contacting the L-shaped ratchet-toothed engagement member biases said L-shaped ratchet-toothed engagement member into engagement with the pawl tooth portion; and wherein, the camming switch and the camming end of the cammed lever member are configured such that when the camming switch is disposed at a first angle relative to the cammed lever member, a first operative contact between the camming switch and the protruding camming surface of the cammed lever member levers the L-shaped ratchet-toothed engagement member out of its biased engagement with the pawl tooth portion of the pawl member; and wherein, the camming switch and the camming end of the cammed lever member are also configured such that when the camming switch is disposed at a second angle relative to the cammed lever member, a second operative contact between the camming switch and the depressed camming surface of the cammed lever member levers the L-shaped ratchet-toothed engagement member out of its biased engagement with the pawl tooth portion of the pawl member.

In yet another aspect, the present invention includes a single-switch release/defeat ratchet mechanism for an in-line surgical instrument handle, the ratchet mechanism comprising: a cam switch member, a pivotable ratchet member in operative contact with the cam switch member, a biasing member, and a pawl member; wherein, when the mechanism is in a ratchet-engaged state, the cam switch member occupies a neutral first position such that the operative contact is minimal and the biasing member biases the ratchet member into engagement with the pawl member; wherein, when the mechanism is in a ratchet-released state, the cam switch member occupies a second position such that the operative contact opposes the bias of the biasing member and releases the ratchet member from engagement with the pawl member; and wherein, when the mechanism is in a ratchet-defeated state, the cam switch member occupies a third position such that the operative contact biases the ratchet member out of engagement with the pawl member.

In still another aspect, the present invention includes an in-line surgical instrument having a handle ratchet mechanism with a single-switch release/defeat feature, the handle ratchet mechanism comprising: a first engagement member; a second engagement member pivotably mounted to a handle portion and projecting toward the first engagement member, a first end portion of the second engagement member being spring-biased into engagement with the first engagement member; and a cam switch movably connected to the handle portion and comprising an operative contact with a second end portion of the second engagement member; wherein, when the cam switch is oriented at a first position relative to the second engagement member, the operative contact is sufficient to pivot the second engagement member so as to overcome the spring-biased engagement of the second engagement member with the first engagement member; and wherein, when the cam switch is oriented at a second position relative to the second engagement member, the operative contact is sufficient to pivot the second engagement member so as to overcome the biased engagement of the second engagement member with the first engagement member and is also sufficient to bias the second engagement member out of engagement with the first engagement member.

In still yet another aspect, the present invention includes an in-line surgical instrument having a handle operatively connected to an elongate shaft, the handle comprising: a first handle member pivotably connected near a proximal end thereof to a second handle member near a proximal end thereof; a ratchet-toothed engagement member comprised by the first handle member; a pawl engagement member pivotably mounted in the second handle member, a portion of the toothed engagement member being biased into engagement with the pawl engagement member; and an elongate camming switch pivotably connected to the first handle member and comprising an operative contact with a surface of the toothed engagement member; wherein, when the elongate camming switch is oriented in a first position relative to the toothed engagement member, the operative contact provides a force sufficient to overcome the biased engagement of the toothed engagement member with the pawl engagement member; and wherein, when the elongate camming switch is oriented in a second position relative to the toothed engagement member, the operative contact is sufficient to pivot the toothed engagement member so as to overcome the biased engagement of the toothed engagement member with the pawl engagement member and is sufficient to bias the toothed engagement member out of engagement with the pawl engagement member.

In still another aspect, the present invention includes an in-line surgical instrument having a handle operatively connected to an elongate shaft, the handle comprising: a ratchet mechanism configured to be engaged, released, and defeated by actuation of a single actuation means.

BRIEF DESCRIPTION OF THE DRAWINGS

FIGS. 1A-1B show a prior art laparoscopic tool device;

DETAILED DESCRIPTION

Figure 2A:
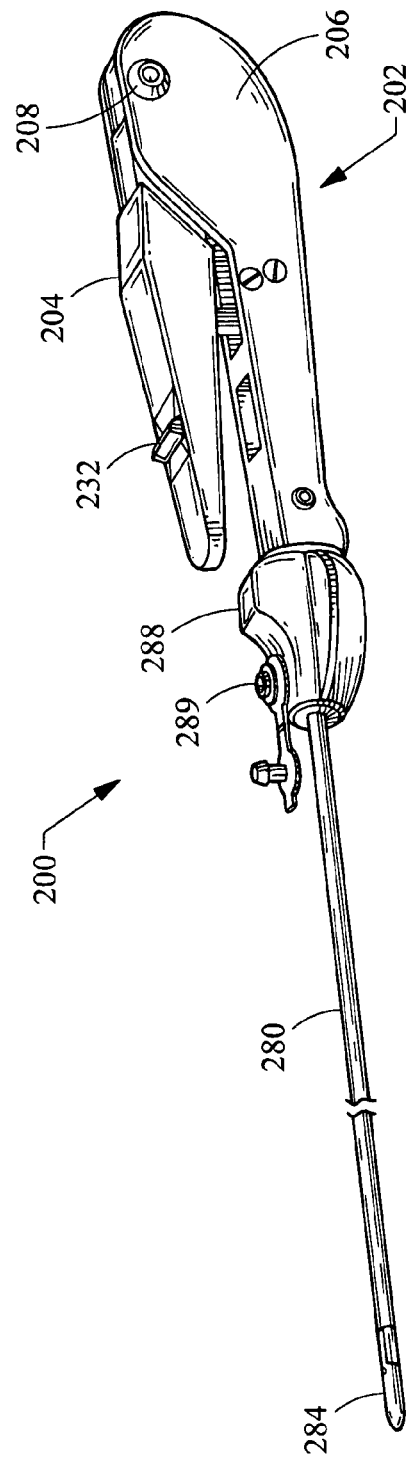
FIGS. 2A-2B illustrate, respectively, perspective and side elevation views of a laparoscopic device incorporating a first handle embodiment of the present invention.
Figure 2B:
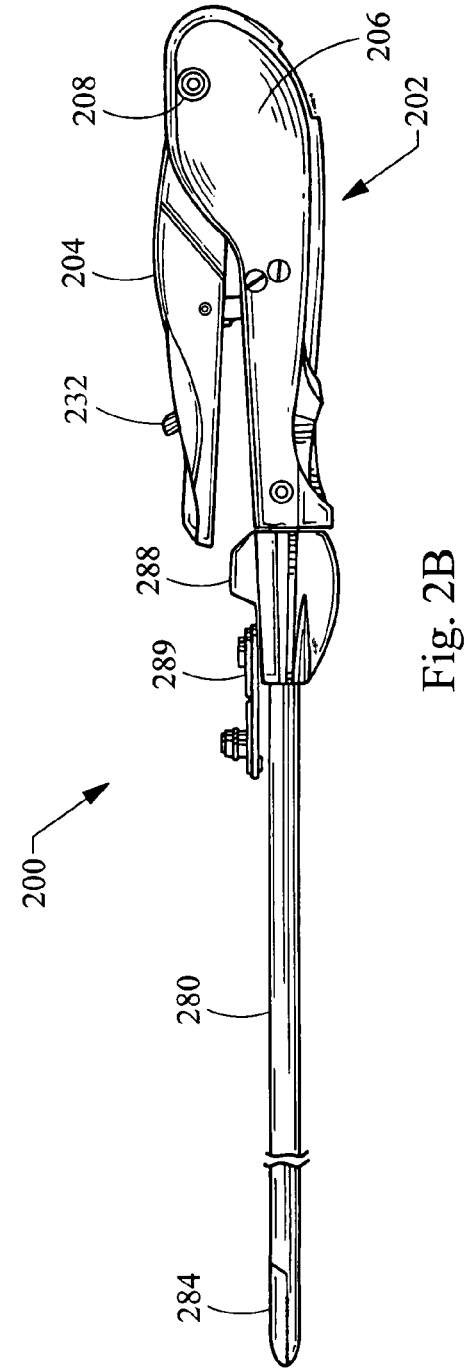

A first embodiment of a handle 202 for a laparoscopy device 200 is illustrated with reference to FIGS. 2A-2B and FIGS. 3-3D. The handle 202 includes a first handle member 204 pivotably attached at a pivot pin 208 to a second handle member 206. The first and second handle members 204, 206 preferably may be constructed of a resin material but may also be constructed of plastic, metal, or other materials known in the art to be suitable for multiple sterilizations in an autoclave. A single-use embodiment may also be constructed of materials known in the art. An elongate tubular shaft 280 extends distally from the second handle member 206, and preferably will be configured to be axially rotatable. An actuation rod 282 extends distally from the first handle member 204 through the shaft 280. At the distal end of the device 200, an end effector 284 (e.g., grasper, scissors, forceps, dissector, needle holder, clamp) is operably connected both to the shaft 280 and the actuation rod 282. Those of skill in the art will appreciate that this configuration provides for actuation of the end effector 284 by pivoting the first handle member 204 relative to the second handle member 206 (see, e.g., U.S. Pat. Nos. 5,498,256 and 5,827,263).

In the embodiment illustrated in FIGS. 2A-3D, a ratchet mechanism 230, embodied as a single-switch release/defeat ratchet mechanism, is mounted in the handle 202 and configured to selectably secure the first handle member 204 at a user-selected angle to the second handle member 206.

Figure 3:
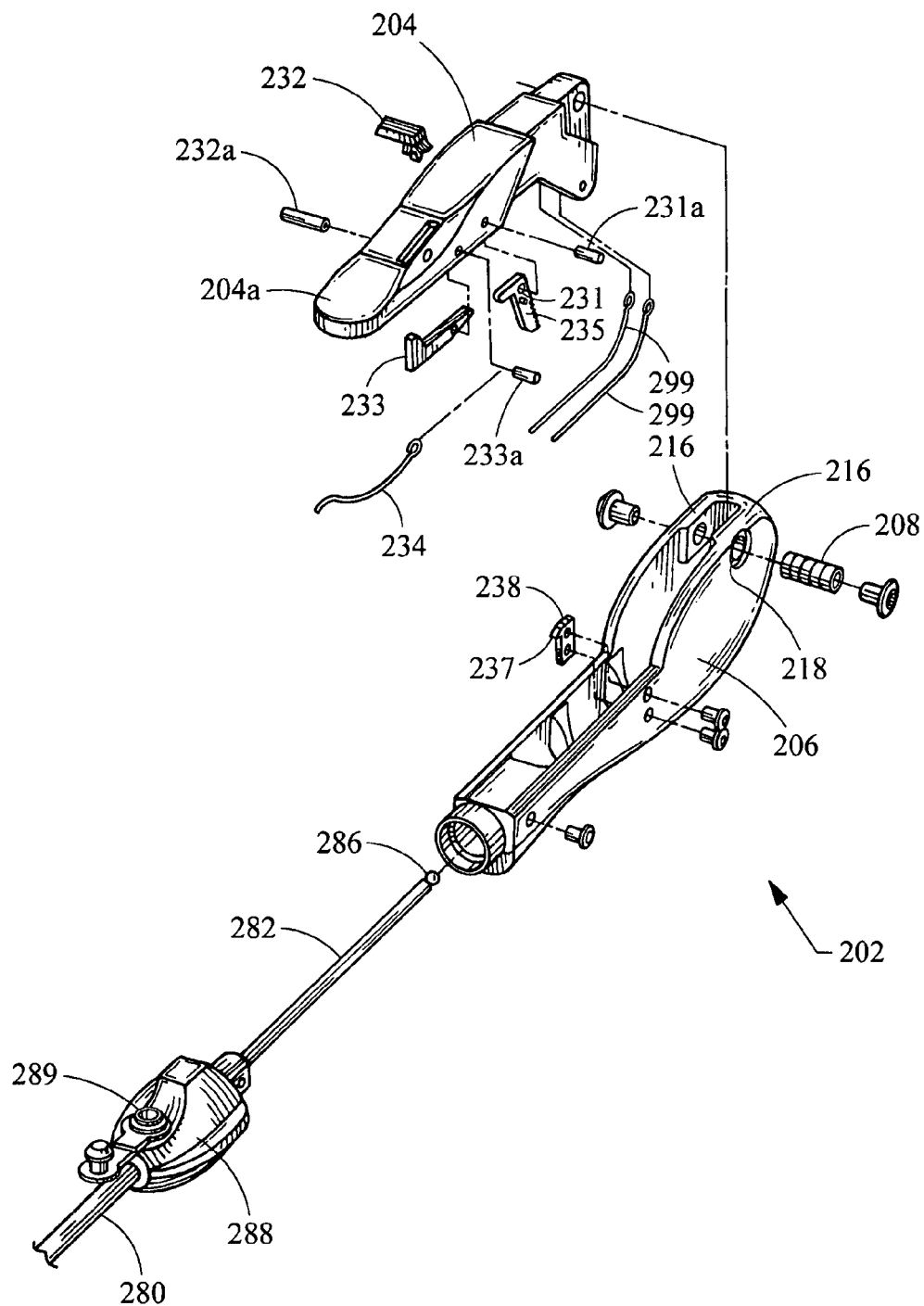
FIG. 3 depicts a perspective view of a partially exploded handle embodiment of the present invention.
Figure 3A:
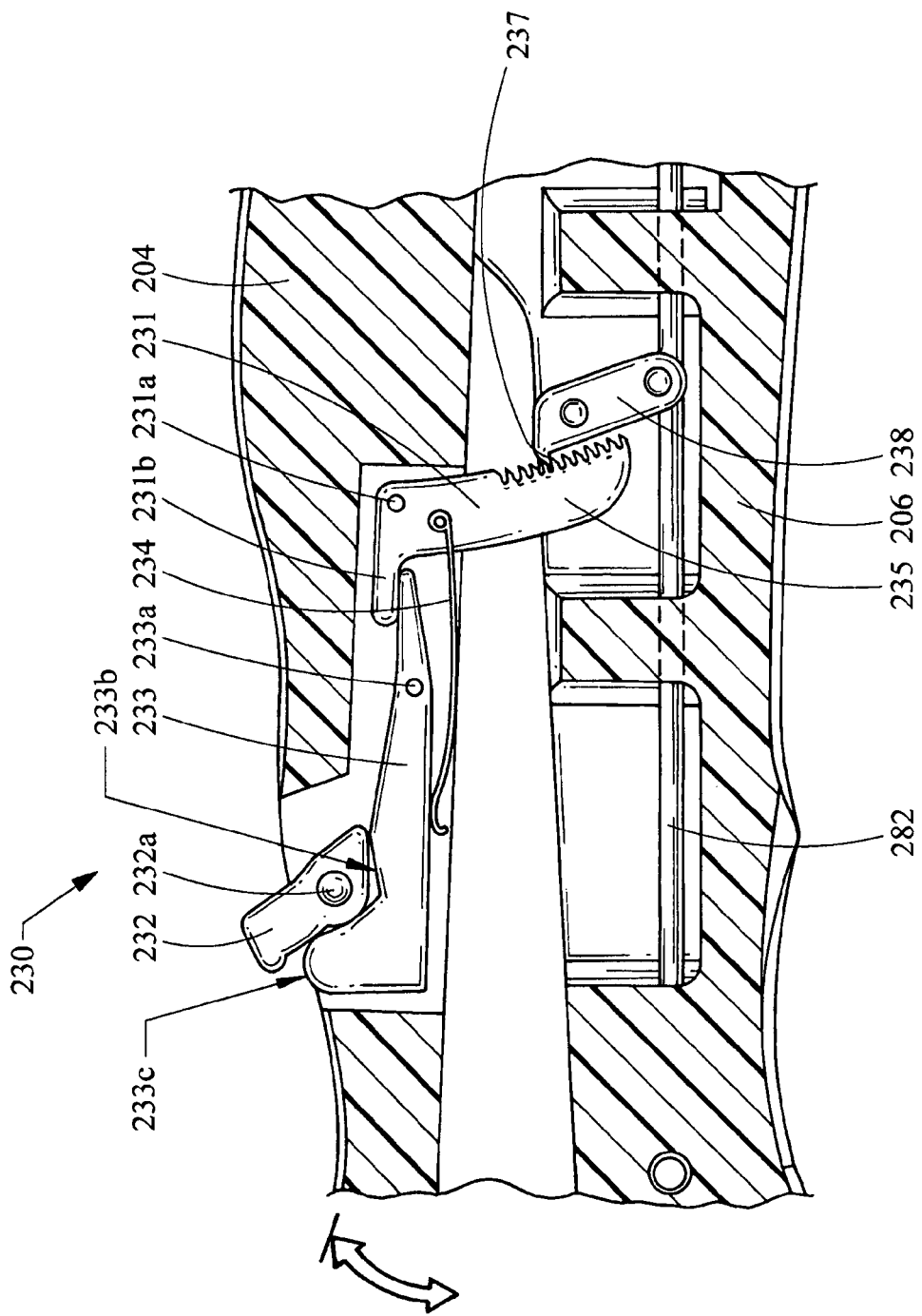
FIGS. 3A-3C show, respectively, engaged, released, and defeated states of a ratchet mechanism of the present invention in a first handle embodiment.
Figure 3B:
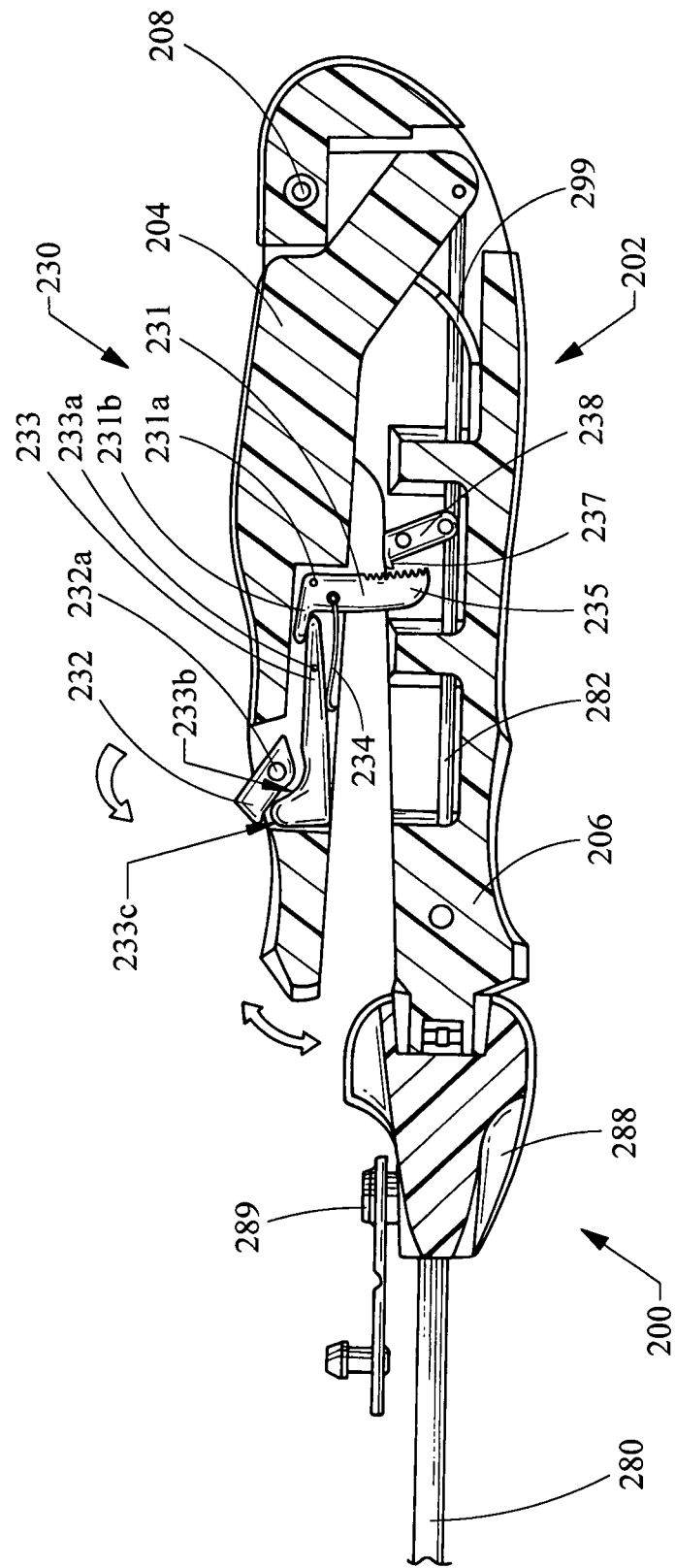
Figure 3C:
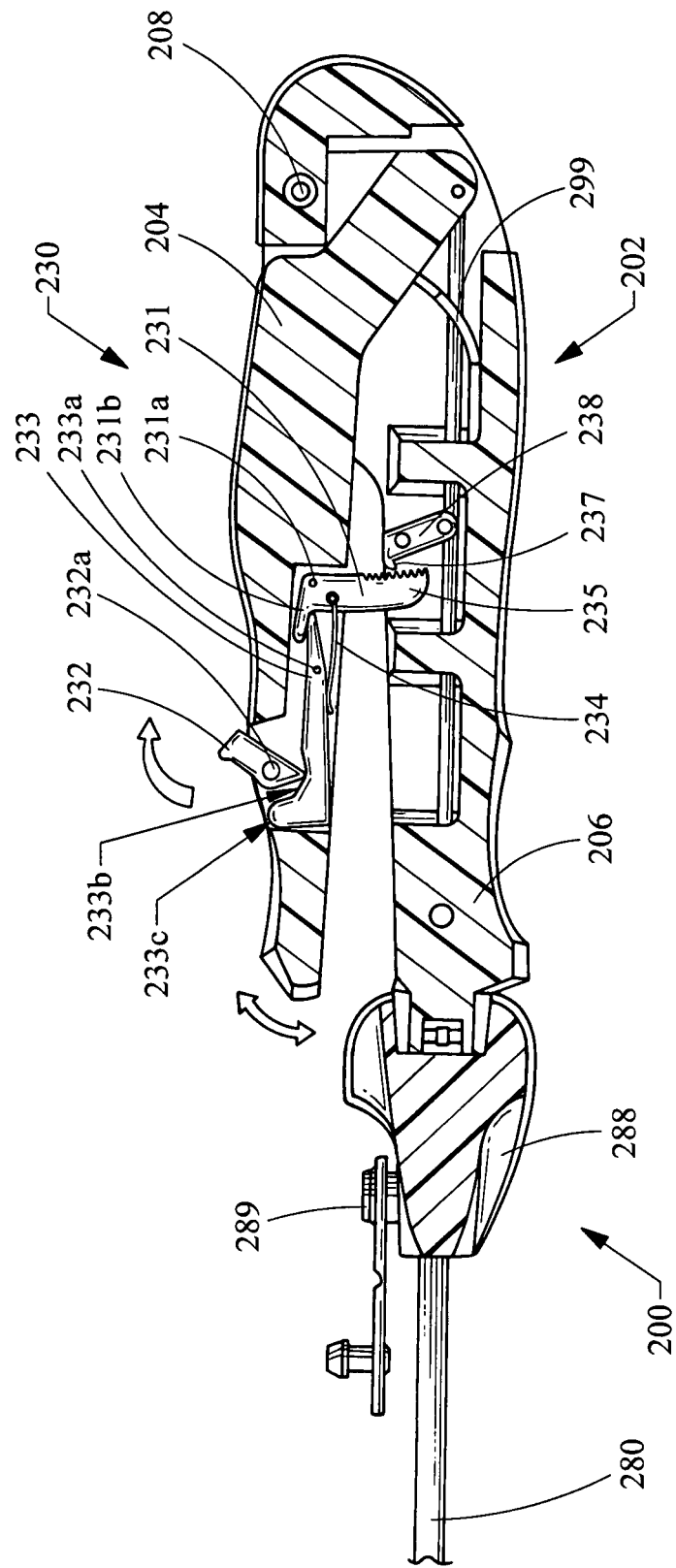
Figure 3D:
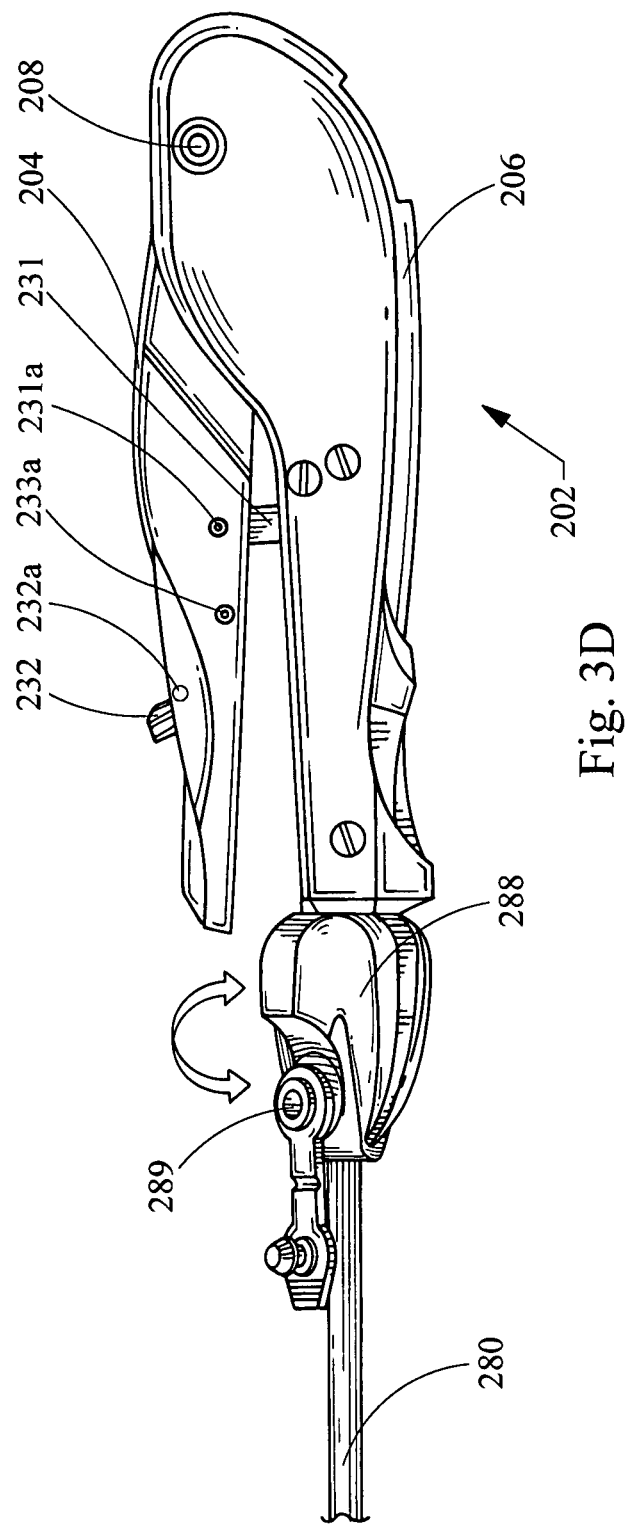
FIG. 3D shows a side view of a handle embodiment of the present invention with an indexed rotation knob being rotated.
Figure 4A:
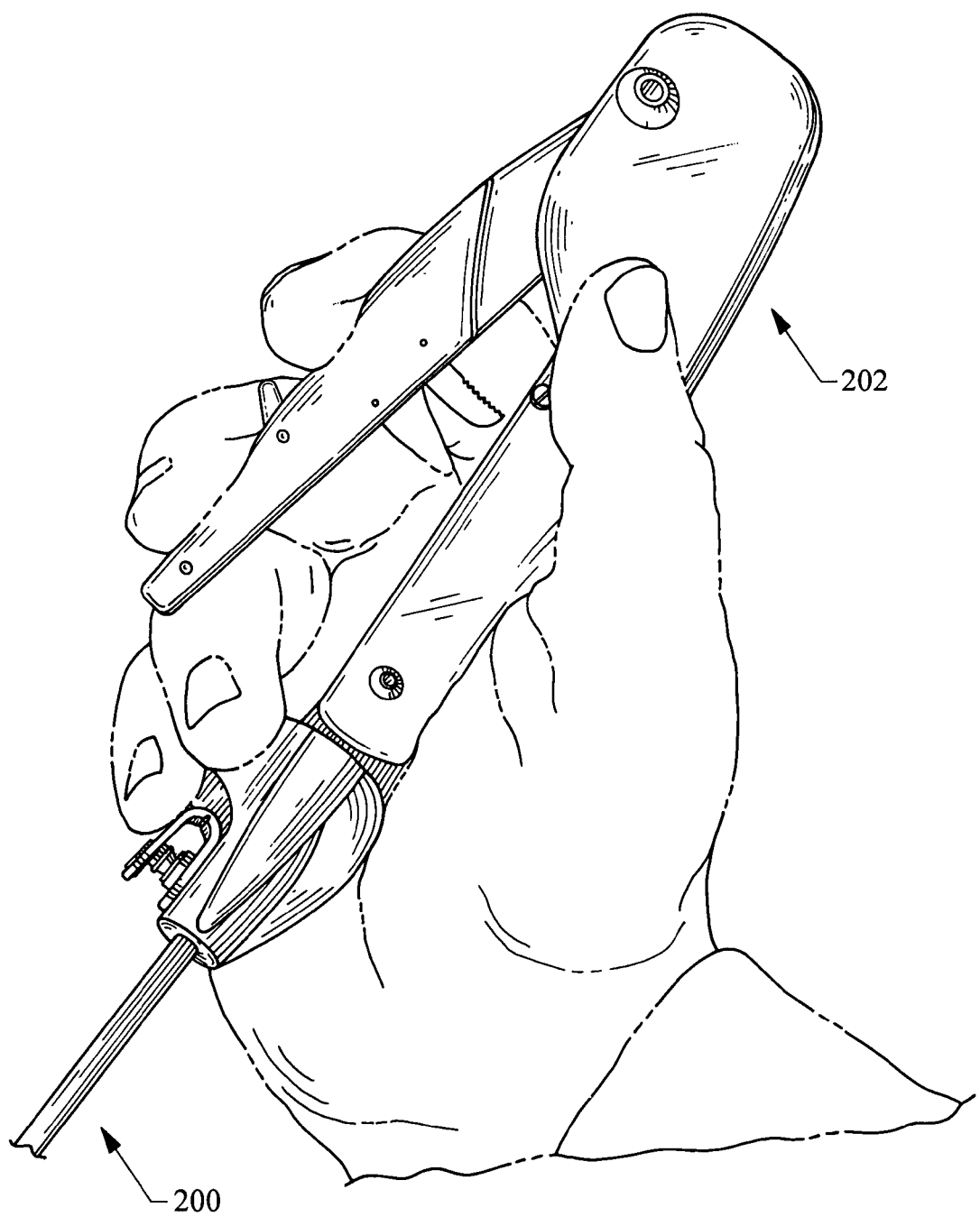
FIGS. 4A-4D depict four of the grips that a user may utilize with the first handle embodiment.
Figure 4B:
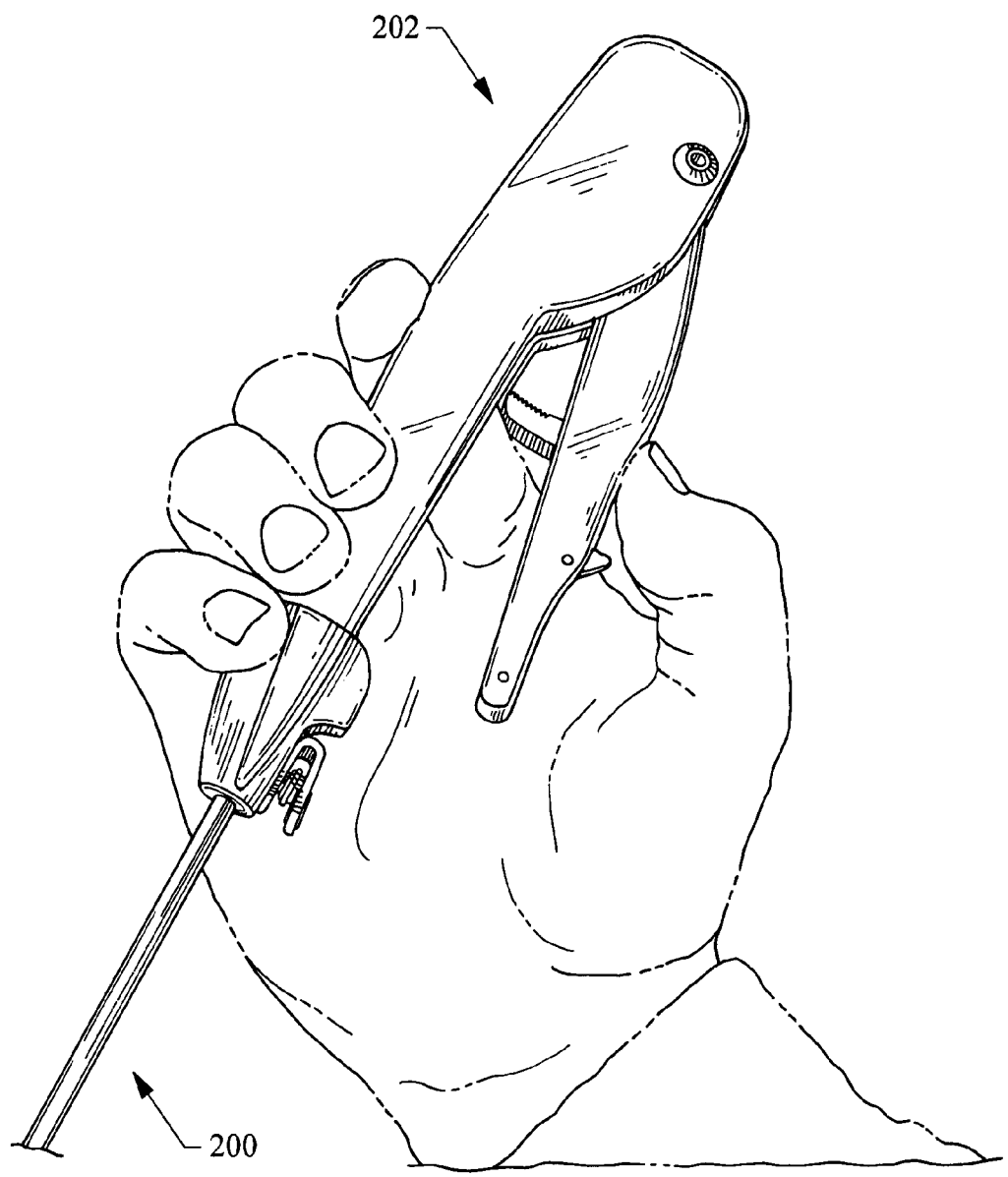
Figure 4C:
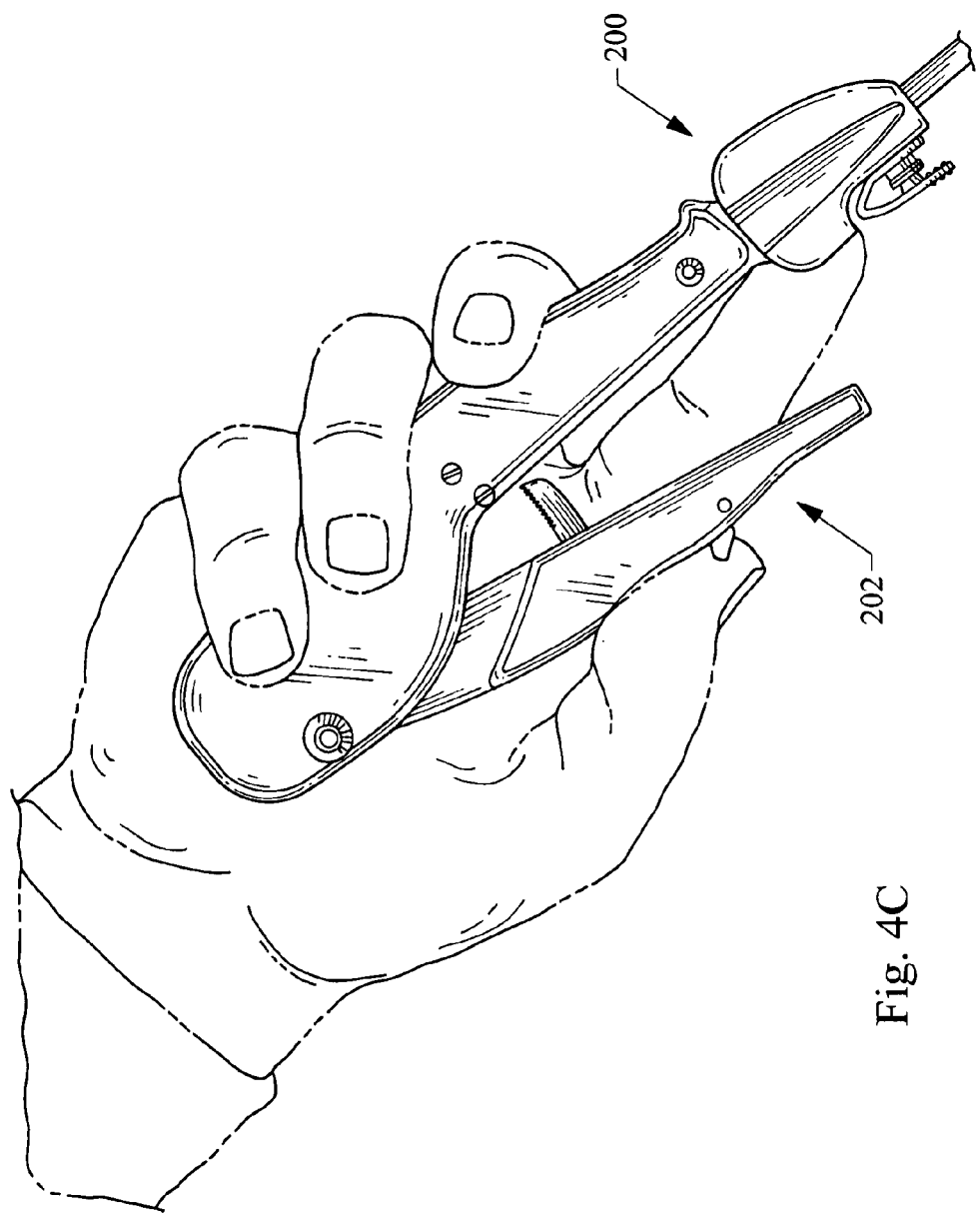
Figure 4D:
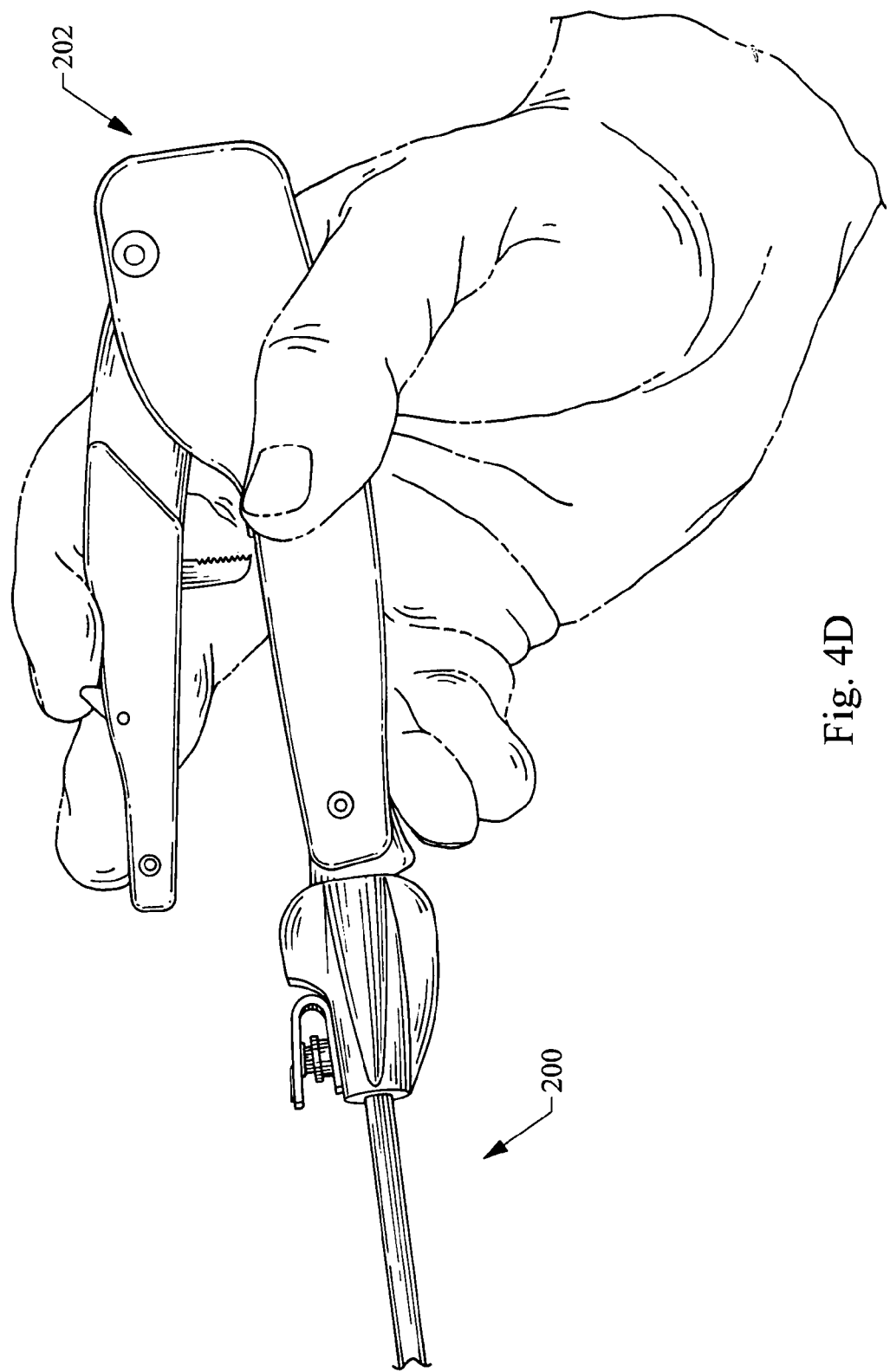

FIG. 3 shows a partially exploded view of the handle 202. FIG. 3A shows a longitudinal section view of a portion of the handle 202, and is magnified to show greater detail of the ratchet mechanism than is depicted in FIGS. 3B-3D, which show the entire handle in longitudinal section. The upper proximal region of the second handle member 206 is constructed to engage the first handle member 204. Specifically, the upper proximal region includes an upwardly-extending pair of arms 216 with a pivot aperture 218 that extends through the arms 216 and that is configured for engaging the pivot pin 208 (depicted as a dual sexbolt) on either side of an upper proximal region of the first handle member 204. The proximal lower region of the first handle member 204 is configured to receive a ball 286 (or other actuation-rod-retaining structure) on the proximal end of the actuation rod 282. The distal upper surface of the first handle member 204 may include a depressed surface 204a configured to aid a user's grip and/or tactile sensory location of the handle end. In the illustrated embodiment, a pair of wire springs 299 (preferably formed of a nickel-titanium shape-memory alloy such as nitinol or another suitable material) may be mounted to the proximal portion of the first handle portion 204 and configured to contact an inner surface of the second handle portion 206 in a manner that biases the first handle portion 204 to pivot away from the second handle portion 206. As a result of this bias, the default position of the handle 202 will be for the handle members 204, 206 to be spread apart. Additionally, this bias may help to maintain engaging tension within a ratchet mechanism 230 (described below) when it is engaged. Those of skill in the art will appreciate that other embodiments configured to bias apart the handles may be practiced within the scope of the present invention such as, for example, one or more compression springs, hinge springs, an elastomeric structure or other biasing means known or developed in the art.

In the embodiment illustrated, an indexed rotation knob 288 rotatably overlaps the distal exterior of the upper region of the second handle member 206 and is attached to the shaft 280. The rotation knob 288 preferably includes a flush port 289 open to the interior of the shaft 280 and configured to provide fluid communication thereto. (See, e.g., U.S. Pat. No. 5,489,290, which is incorporated herein by reference, for illustration of a representative flush port/rotation knob mechanism). The rotation knob 288 provides means for rotating the shaft 280 about its longitudinal axis, relative to the handle 202. The knob 288 preferably is disposed in an ergonomically-oriented position such that a user may rotate it without removing or significantly altering his/her grip on the handle 202, and its outer surface preferably includes a plurality of broad grooves to provide purchase for the user's finger. Rotation of the shaft by rotating the knob 288 preferably will be indexed (for example, by use of a ball detent) to allow precise, controlled rotation of the shaft 280 that may be in a smooth or an incremental manner. By way of illustration, FIG. 3D shows an external side view of the handle 202 with the knob 288 rotated at an angle. Those of skill in the art will appreciate that other embodiments may be configured for use as a monopolar or bipolar electrosurgical instruments (e.g., by providing an electrode and appropriately insulated surfaces as is known in the art) within the scope of the present invention.

The handle 202 includes a ratchet mechanism 230, described with reference to FIGS. 3A-3C, the design of which provides advantages for assembly of the device 200 and ease of use. An inverted-L-shaped ratchet-toothed member 231 is pivotably mounted (on a transverse pivot pin 231a) in the first handle member 204, together with a release/defeat camming lever or camming switch (which are used as equivalents herein)—shown here as a camming switch 232—a cammed lever 233 that provides mechanical communication between the camming switch 232 and the ratchet-toothed member 231. A leaf spring 234 may be mounted at one end to the ratchet-toothed member 231 to bias it (231) against the cammed lever 233, and to bias the cammed lever 233 into contact with the camming switch 232. A pawl member 238 is disposed in the second handle member 206 opposite the ratchet-toothed member 231. The ratchet-toothed member 231 includes a slightly curved toothed projection 235 that extends out of the first handle member 204 toward the second handle member 206. The pawl member 238 extends toward the first handle member 204 and includes a pawl tooth 237 that is configured to engage teeth on the toothed projection 235 of the ratchet-toothed member 231. The cammed lever 233 also includes a depressed first camming surface 233b on its upper side and a protruding second camming surface 233c extending above and distally from the first camming surface 233b. Those of skill in the art will appreciate that the biasing means embodied as leaf spring 234 may take other forms in other embodiments within the scope of the present invention, such as, for example, a compression or coil spring oriented adjacent any of the above-described components to provide the desired bias, or an elastomeric member configured to provide the desired bias.

The proximal end of the leaf spring 234 is secured to the ratchet-toothed member 231 below that member's pivot pin 231a and oriented such that its distal contact surface contacts the lower side of the cammed lever 233 distal of its (233) fulcrum/pivot axis at mounting/pivot pin 233a, thereby simultaneously biasing the distal portion of the cammed lever 233 generally upward and biasing the lower portion (below the pivot pin 231a) of the ratchet-toothed member 231 generally proximally. The camming switch 232 is pivotably attached to the first handle member 206 by a cam switch pivot pin 232a. In an alternative embodiment, the relative positions of the ratchet-toothed member 231 and the pawl member 238 may be reversed (for example, such that the pawl member is pivotably disposed in the first handle member and the ratchet toothed member is disposed in the second handle member). Those of skill in the art will appreciate that this reversibility of the complementary/engaging surfaces is applicable to other embodiments of the present invention and that other variations of the illustrated embodiments may be practiced within the scope of the present invention. Those of skill in the art will also appreciate that, within the scope of the present invention, the entire mechanism may also be reversed in orientation— such as, for example, with the camming switch 232 and either a pawl or ratchet-toothed member being disposed in the non-pivoting handle member.

The ratchet mechanism 230 can be actuated to one of three user-selected states (engaged, released, and defeated), which are described, respectively, with reference to FIGS. 3A, 3B, and 3C.

As shown in FIG. 3A, when the ratchet mechanism 230 is in an engaged state, the teeth of the ratchet-toothed projection 235 engage the pawl tooth 237 of the pawl member 238. This engagement prevents the first handle 204 from being moved away from the second handle 206 (e.g., by the handle-separating bias of the wire springs 299), but allows it to be moved closer to the second handle 206 with auditory and tactile feedback as the ratchet teeth move incrementally across the pawl tooth 237. In the engaged state, pawl tooth contact with the ratchet-toothed projection 235 of the ratchet-toothed member 231 is maintained by the bias of the leaf spring 234 against the underside of the cammed lever 233. This leaf spring bias exerts a proximal force against the portion of the ratchet-toothed member 231 (below its pivot axis 231a), thereby pivoting the ratchet-toothed member 231 about its pivot axis 231a such that the curved, toothed projection 235 is directed proximally into engagement with the pawl tooth 237 of the pawl member 238 in the second handle member 206. When the handle 202 is in the engaged position, the camming switch 232 is at rest (in a neutral central position in the illustrated embodiment) and does not have significant operative contact with the cammed lever 233. In the illustrated embodiment the bias-apart effect of the wire springs 299 on the handle members 204, 206 provides a tension that may help to maintain a contact tension between the ratchet-toothed member 231 and the pawl member 238.

As shown in FIG. 3B, when the ratchet mechanism 230 is in a released state, the teeth of the ratchet-toothed projection 235 are disengaged from the pawl tooth 237 of the pawl member 238. This disengagement allows the first handle 204 freely to be moved toward or away from the second handle 206. The released state is effected by pivoting the upper end of the camming switch 232 in a distal direction. When pivoted thus, the camming switch 232 is dynamically held in operative contact against the protruding second camming surface 233c of the cammed lever 233. This contact levers downward the distal portion of the cammed lever 233 (distal of the cammed lever pivot pin 233a) against the bias of the leaf spring 234. Consequently, a proximal portion of the cammed lever 233 is levered upward against an upper distal projection 231b of the ratchet toothed member 231, thereby levering it (231) to rotate about its pivot pin 231a such that its lower portion (the ratchet-toothed projection 235) pivots distally and out of engagement with the pawl tooth 237 of the pawl member 238 in the second handle member 206. In order to maintain the released state, the camming switch 232 must be held in the rotated-distal/forward position (to resist the bias of the leaf spring 234). Releasing the camming switch 232 allows the bias of the leaf spring 234 to return the ratchet mechanism 230 to its engaged state.

The ratchet mechanism 230 is in a defeated state in FIG. 3C, wherein the ratchet-toothed projection 235 is disengaged from the pawl tooth 237 of the pawl member 238, allowing the handle portions 204, 206 to travel through a full range of motion without engagement of the ratchet mechanism 230, and without a user exerting dynamic pressure on the camming switch 232 (as is required in the released state). The defeated state is effected by pivoting the upper end of the camming switch 232 into a proximal position. In this defeated state, the lower portion of the camming switch 232 is locked in operative contact against the depressed first camming surface 233b of the cammed lever 233. This contact levers downward the distal portion of the cammed lever 233 (distal of the cammed lever pivot pin 233a) against the bias of the leaf spring 234. Consequently, a proximal portion of the cammed lever 233 is levered upward against the distal projection 231b of the ratchet toothed member 231, thereby levering it to rotate about its pivot pin 231a such that its lower portion (the ratchet-toothed projection 235) will pivot distally and out of engagement with the pawl tooth 237 of the pawl member 238 in the second handle member 206. The "locked" status of the camming switch 232 in the defeated state is effected by the upward bias of the leaf spring 234 on the cammed lever 233 against the camming switch 232. Specifically the camming switch is locked into a proximally rotated position as its lower portion (below the pivot pin 232a) is pivoted past a point of inflection such that the depressed first cam-engaging surface 233b contacts the camming switch 232 and the upward bias of the leaf spring 234 on the cammed lever 233 against the camming switch 232 effectively enables the depressed first cam-engaging surface 233b to capture the lower portion of the camming switch 232.

Those of skill in the art will appreciate that the handle 202 may be allowed to be sufficiently open such that the ratchet-toothed member 231 is longitudinally separated from the pawl member 238 and positioning the camming switch 232 at an angle associated with the engaged, released, or defeated states will prepare the handle for a desired state when the handle members 204, 206 are pivoted toward each other. Those of skill in the art will also appreciate that, in other embodiments within the scope of the present invention, a camming switch may be configured to roll or slide relative to the cammed lever 233 rather than pivoting, and/or a camming switch (such as, for example, the camming switch 232) may be configured to have a direct operative contact with a ratchet-toothed member or a pawl member together with, or in the absence of a cammed lever.

FIGS. 4A-4D show four examples of grip positions that a user may utilize with the device 200 having a handle 202. These grips may be selected based upon one or more of a user's style, personal preference; comfort, necessity of orientation angle (such as, for example, due to port placement and/or trocar angle during a laparoscopic procedure), or any other reason a user may wish to utilize or alter his/her grip. Those of skill in the art will appreciate that the handle shape and the position and function of the ratchet mechanism 231 described above present advantages for a user to operate the device from a variety of angles and positions during a procedure such as, for example, a laparoscopic bariatric surgical procedure. Specifically, those of skill in the art will appreciate that users may choose variants of the grips shown, or may use other grips, but that virtually all practical grip positions will provide for easy actuation of the ratchet mechanism 230 without the user significantly altering his/her grip and without requiring another hand to actuate the ratchet mechanism 230 using the camming switch 232.

Figure 5A:
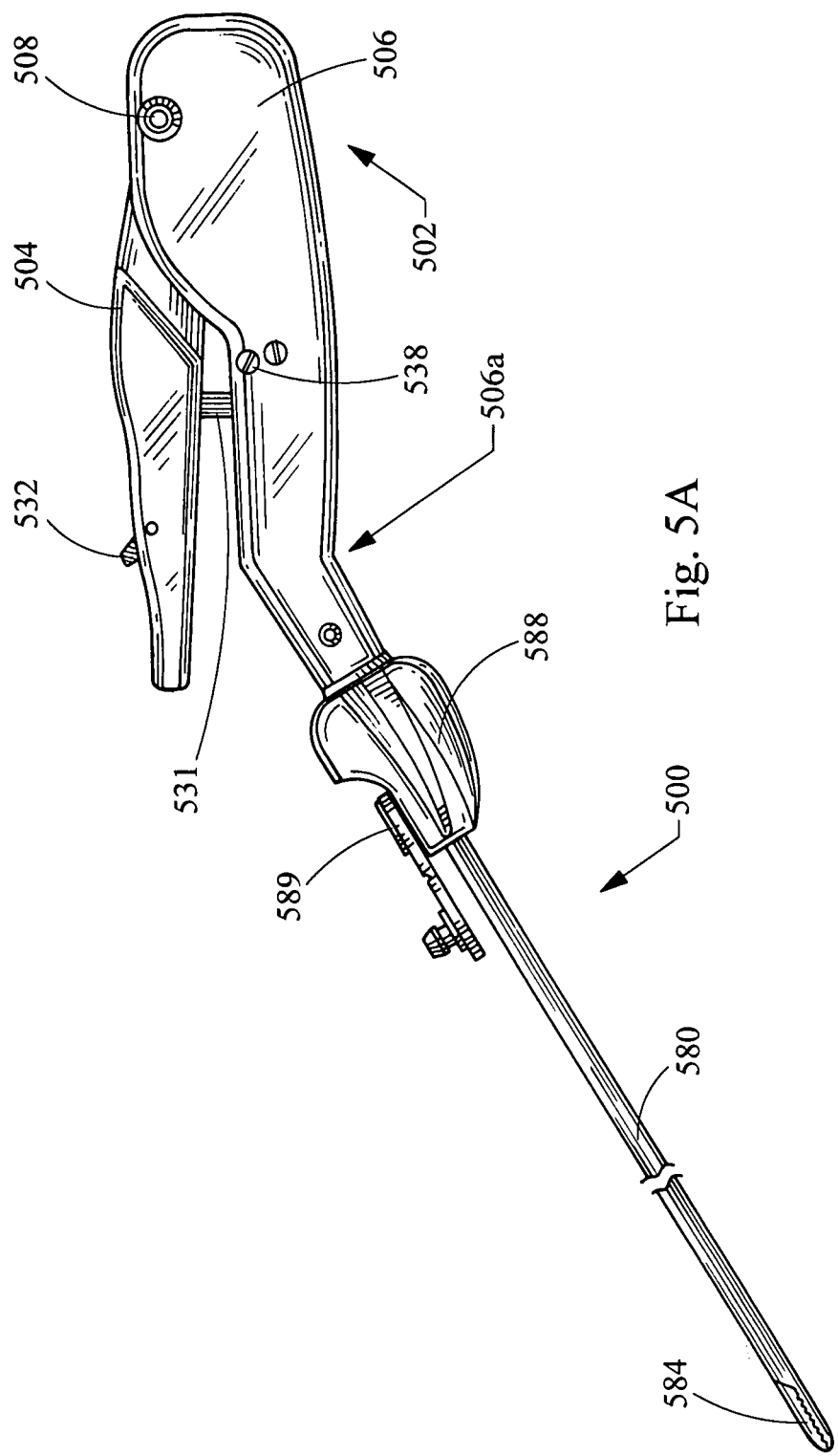
FIGS. 5A-5B illustrate, respectively, side elevation and perspective views of a laparoscopic device incorporating a second handle embodiment of the present invention.
Figure 5B:
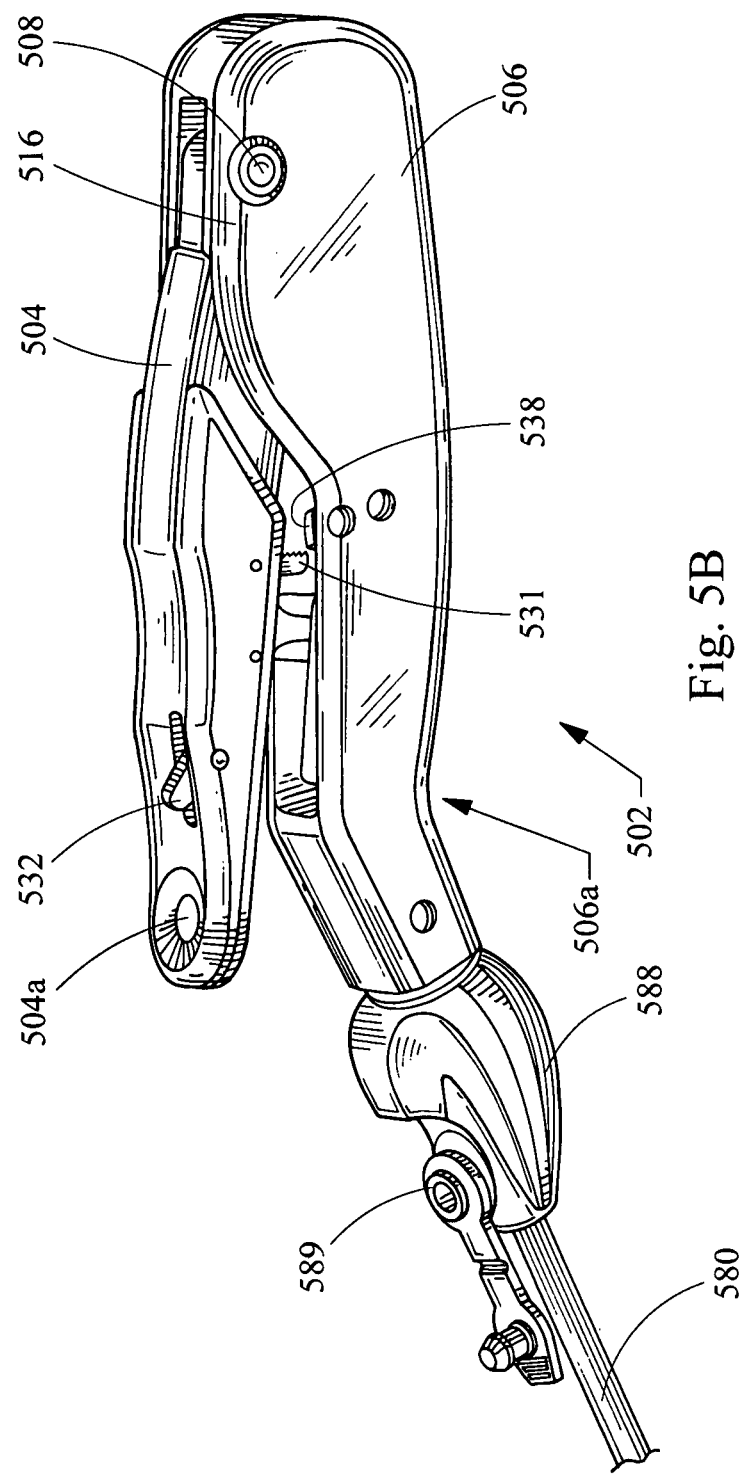

A second embodiment of a handle 502 for a laparoscopy device 500 is illustrated with reference to FIGS. 5A-5B and FIGS. 6A-6C. FIG. 5A shows a side view of the device 500, and FIG. 5B shows a top perspective view of the device handle 502. The handle 502 includes a first handle member 504 pivotably attached at a pivot pin 508 to a second handle member 506. The first and second handle members 504, 506 preferably may be constructed of a resin material but may also be constructed of plastic, metal, or other materials known in the art to be suitable for multiple sterilizations in an autoclave. A single-use embodiment may also be constructed of materials known in the art. An elongate tubular shaft 580 extends distally from the second handle member 506, and preferably will be configured to be axially rotatable. An actuation rod 582 extends distally from the first handle member 504 through the shaft 580. At the distal end of the device 500, an end effector 584 (e.g., a tool tip such as, for example, grasper, scissors, forceps, dissector, clamp, needle holder) is operably connected both to the shaft 580 and the actuation rod 582. Those of skill in the art will appreciate that this configuration provides for actuation of the end effector 584 by pivoting the first handle member 504 relative to the second handle member 506 (see, e.g., U.S. Pat. Nos. 5,498,256 and 5,827,263).

The handle embodiment 502 may be substantially similar to the handle embodiment 202 described above, except that the second handle member 506 includes a distal bend 506a configured to allow a user the ability to exert a desired rotational torque for rotating the distal tool tip 584. Accordingly, a transition member 582a and rod anchor member 582b are included between the proximal end of the actuation rod 582 and the first handle member 504, and are configured for transmitting longitudinal motion from the handle 502 through the actuation rod 582 to the tool tip 584. Those of skill in the art will appreciate that this handle configuration may be particularly well adapted for use with, for example, a laparoscopic needle grasper used for suturing with a curved needle wherein a user desires to rotate the shaft and tip about a longitudinal axis. It should also be appreciated that, for the purpose of this application, the term "in-line surgical instrument" includes the embodiments of all of FIGS. 2A-6C, whether the handle portion is strictly axial or includes the angled offset of FIGS. 5A-6C.

In the embodiment illustrated in FIGS. 6A-6D, a ratchet mechanism 530, embodied as a single-switch release/defeat ratchet mechanism, is mounted in the handle 502 and configured to selectably secure the first handle member 504 at a user-selected angle to the second handle member 506.

Figure 6A:
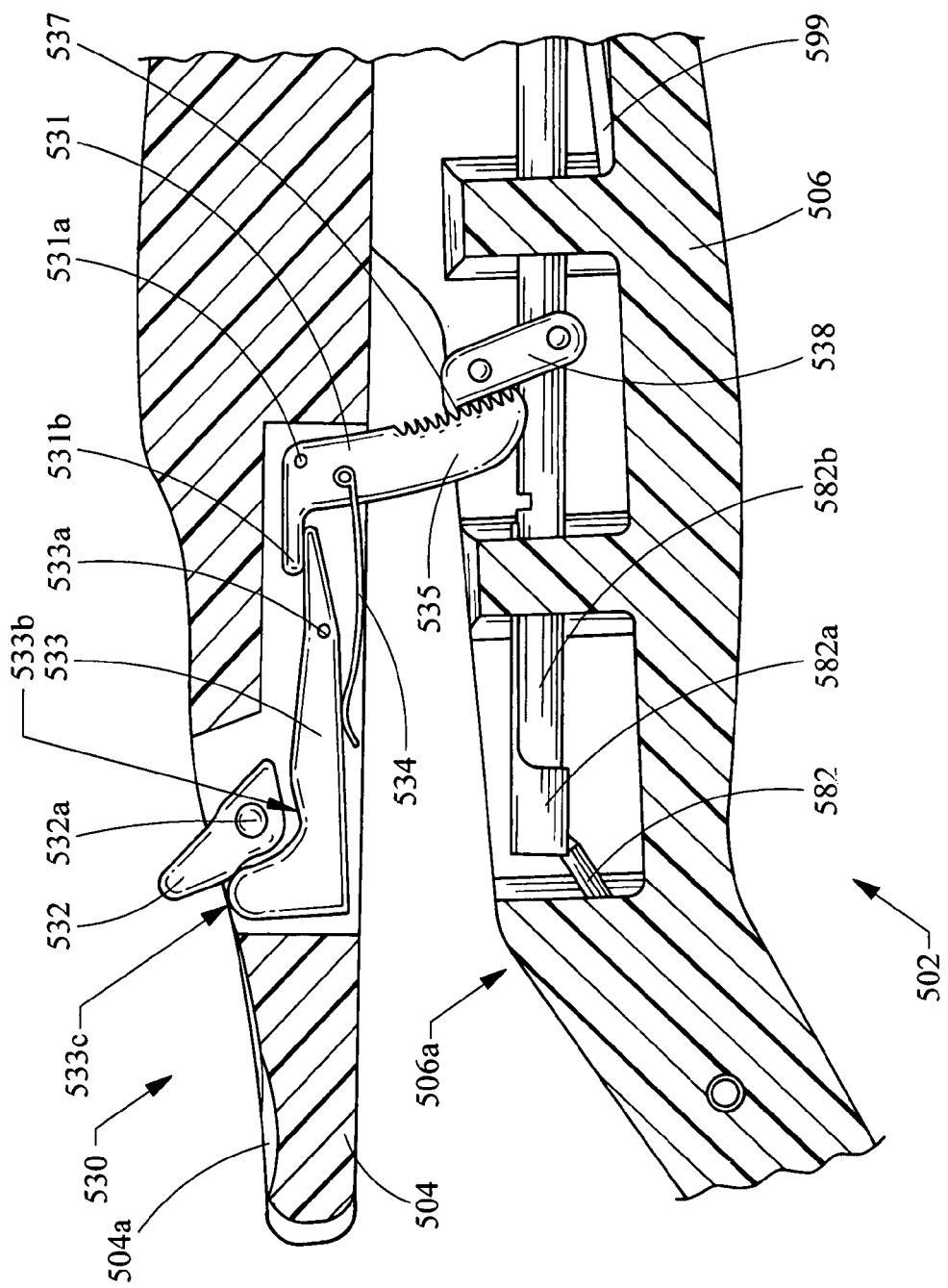
FIGS. 6A-6C show, respectively, engaged, released, and defeated states of a ratchet mechanism of the present invention in a second handle embodiment.
Figure 6B:
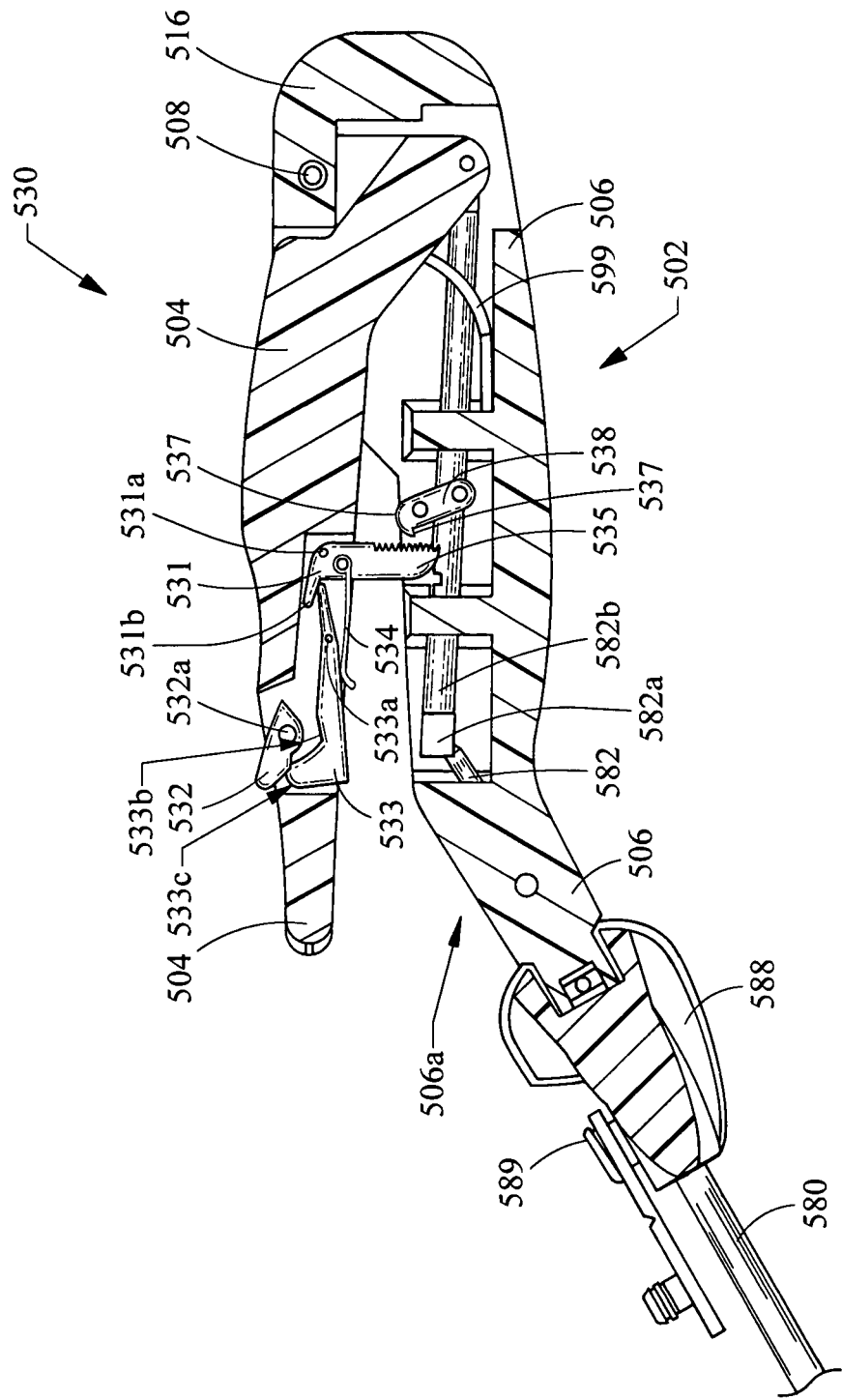
Figure 6C:
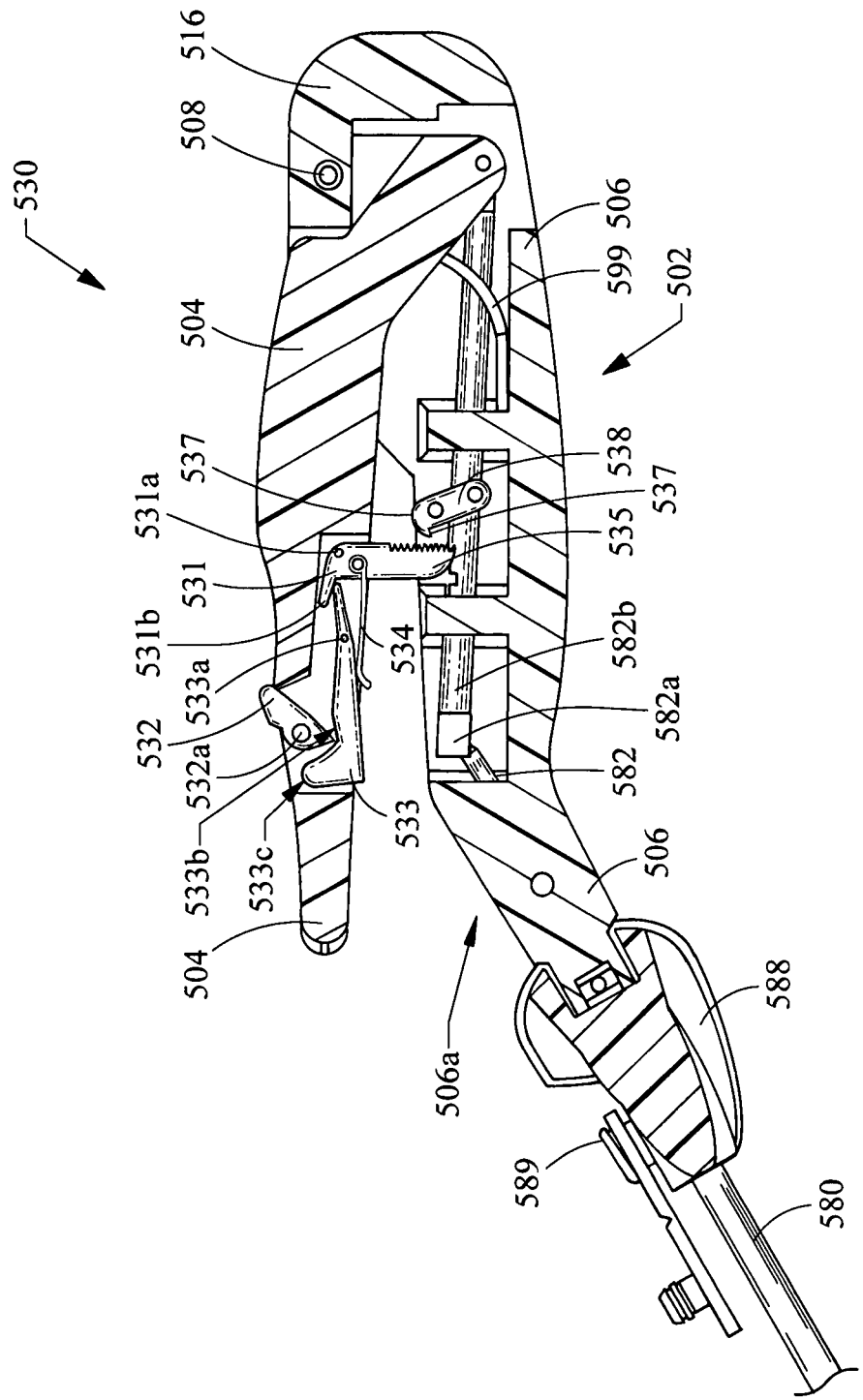

FIG. 6 shows a partially exploded view of the handle 502. FIG. 6A shows a longitudinal section view of a portion of the handle 502, and is magnified to show greater detail of the ratchet mechanism than is depicted in FIGS. 6B-6C, which show the entire handle in longitudinal section. The upper proximal region of the second handle member 506 is constructed to engage the first handle member 504. Specifically, the upper proximal region includes an upwardly-extending pair of arms 516 with a pivot aperture 518 that extends through the arms 516 and that is configured for engaging the pivot pin 508 (depicted as a dual sexbolt) on either side of an upper proximal region of the first handle member 504. The proximal lower region of the first handle member 504 is configured to receive a ball 586 (or other actuation-rod-retaining structure) on the proximal end of the actuation rod 582. The distal upper surface of the first handle member 504 may include a depressed surface 504a configured to aid a user's grip and/or tactile sensory location of the handle end. In the illustrated embodiment, a pair of wire springs 599 (preferably formed of a nickel-titanium shape-memory alloy or another suitable material) may be mounted to the proximal portion of the first handle portion 504 and configured to contact an inner surface of the second handle portion 506 in a manner that biases the first handle portion 504 to pivot away from the second handle portion 506. As a result of this bias, the default position of the handle 502 will be for the handle members 504, 506 to be spread apart. Additionally, this bias may help to maintain engaging tension within a ratchet mechanism 530 (described below) when it is engaged.

In the embodiment illustrated, an indexed rotation knob 588 rotatably overlaps the distal exterior of the upper region of the second handle member 506 and is attached to the shaft 580. The rotation knob 588 preferably includes a flush port 589 open to the interior of the shaft 580. (See, e.g., U.S. Pat. No. 5,489,290, which is incorporated herein by reference, for illustration of a representative flush port/rotation knob mechanism). The rotation knob 588 provides means for rotating the shaft 580 about its longitudinal axis, relative to the handle 502. The knob 588 preferably is disposed in an ergonomically-oriented position such that a user may rotate it without removing or significantly altering his/her grip on the handle 502, and its outer surface preferably includes a plurality of broad grooves to provide purchase for the user's finger. Rotation of the shaft by rotating the knob 588 preferably will be indexed (for example, by use of a ball detent) to allow precise, controlled rotation of the shaft 580 that may be in a smooth or an incremental manner.

The handle 502 includes a ratchet mechanism 530, described with reference to FIGS. 6A-6C, the design of which provides advantages for assembly of the device 500 and ease of use. An inverted-L-shaped ratchet-toothed member 531 is pivotably mounted (on a transverse pivot pin 531a) in the first handle member 504, together with a release/defeat switch—shown here as a camming switch 532, a cammed lever 533 that provides mechanical communication between the camming switch 532 and the ratchet-toothed member 531. A leaf spring 534 mounted at one end to the ratchet-toothed member 531 biases it (531) against the cammed lever 533, and biases the cammed lever 533 into contact with the camming switch 532. A pawl member 538 is disposed in the second handle member 506 opposite the ratchet-toothed member 531. The ratchet-toothed member 531 includes a slightly curved toothed projection 535 that extends out of the first handle member 504 toward the second handle member 506. The pawl member 538 extends toward the first handle member 504 and includes a pawl tooth 537 that is configured to engage with teeth of the toothed projection portion 535 of the ratchet-toothed member 531. The cammed lever 533 also includes a depressed first camming surface 533b on its upper side and a protruding second camming surface 533c extending above and distally from the first camming surface 533b.

The proximal end of the leaf spring 534 is secured to the ratchet-toothed member 531 below that member's pivot pin 531a and oriented such that its distal contact surface contacts the lower side of the cammed lever 533 distal of its (533) pivot axis at mounting/pivot pin 533a, thereby simultaneously biasing the distal portion of the cammed lever 533 generally upward and biasing the lower portion (below the pivot pin 531a) of the ratchet-toothed member 531 generally proximally. The camming switch 532 is pivotably attached to the first handle member 506 by a cam switch pivot pin 532a. In an alternative embodiment, the relative positions of the ratchet-toothed member 531 and the pawl member 538 may be reversed (such that the pawl member is pivotably disposed in the first handle member and the ratchet toothed member is disposed in the second handle member). Those of skill in the art will appreciate that this reversibility of the complementary/engaging surfaces is applicable to other embodiments of the present invention and that other variations of the illustrated embodiments may be practiced within the scope of the present invention.

The ratchet mechanism 530 can be actuated to one of three user-selected states (engaged, released, and defeated), which are described, respectively, with reference to FIGS. 6A, 6B, and 6C.

As shown in FIG. 6A, when the ratchet mechanism 530 is in an engaged state, the teeth of the ratchet-toothed projection 535 engage the pawl tooth 537 of the pawl member 538. This engagement prevents the first handle 504 from being moved away from the second handle 506 (e.g., by the handle-separating bias of the wire springs 599), but allows it to be moved closer to the second handle 506 with auditory and tactile feedback as the ratchet teeth move incrementally across the pawl tooth 537. In the engaged state, pawl tooth contact with the ratchet-toothed projection 535 of the ratchet-toothed member 531 is maintained by the bias of the leaf spring 534 against the underside of the cammed lever 533. This leaf spring bias exerts a proximal force against the portion of the ratchet-toothed member 531 (below its pivot axis 531a), thereby pivoting the ratchet-toothed member 531 about its pivot axis 531a such that the curved, toothed projection 535 is directed proximally into engagement with the pawl tooth 537 of the pawl member 538 in the second handle member 506. When the handle 502 is in the engaged position, the camming switch 532 is at rest (in a neutral central position in the illustrated embodiment) and does not have significant operative contact with the cammed lever 533. In the illustrated embodiment the bias-apart effect of the wire springs 599 on the handle members 504, 506 provides a tension that may help to maintain a contact tension between the ratchet-toothed member 531 and the pawl member 538.

As shown in FIG. 6B, when the ratchet mechanism 530 is in a released state, the teeth of the ratchet-toothed projection 535 are disengaged from the pawl tooth 537 of the pawl member 538. This disengagement allows the first handle 504 freely to be moved toward or away from the second handle 506. The released state is effected by pivoting the upper end of the camming switch 532 in a distal direction. When pivoted thus, the camming switch 532 is dynamically held in operative contact against the protruding second camming surface 533c of the cammed lever 533. This contact levers downward the distal portion of the cammed lever 533 (distal of the cammed lever pivot pin 533a) against the bias of the leaf spring 534. Consequently, a proximal portion of the cammed lever 533 is levered upward against an upper distal projection 531b of the ratchet toothed member 531, thereby levering it (531) to rotate about its pivot pin 531a such that its lower portion (the ratchet-toothed projection 535) pivots distally and out of engagement with the pawl tooth 537 of the pawl member 538 in the second handle member 506. In order to maintain the released state, the camming switch 532 must be held in the rotated-distal/forward position (to resist the bias of the leaf spring 534). Releasing the camming lever 532 allows the bias of the leaf spring 534 to return the ratchet mechanism 530 to its engaged state.

The ratchet mechanism 530 is in a defeated state in FIG. 6C, wherein the ratchet-toothed projection 535 is disengaged from the pawl tooth 537 of the pawl member 538, allowing the handle portions 504, 506 to travel through a full range of motion without engagement of the ratchet mechanism 530, and without a user exerting dynamic pressure on the camming switch 532 (as is required in the released state). The defeated state is effected by pivoting the upper end of the camming switch 532 into a proximal position. In this defeated state, the lower portion of the camming switch 532 is locked in operative contact against the depressed first camming surface 533b of the cammed lever 533. This contact levers downward the distal portion of the cammed lever 533 (distal of the cammed lever pivot pin 533a) against the bias of the leaf spring 534. Consequently, a proximal portion of the cammed lever 533 is levered upward against the distal projection 531b of the ratchet toothed member 531, thereby levering it to rotate about its pivot pin 531a such that its lower portion (the ratchet-toothed projection 535) will pivot distally and out of engagement with the pawl tooth 537 of the pawl member 538 in the second handle member 506. The "locked" status of the camming switch 532 in the defeated state is effected by the upward bias of the leaf spring 534 on the cammed lever 533 against the camming switch 532. Specifically the camming switch is locked into a proximally rotated position as its lower portion (below the pivot pin 532a) is pivoted past a point of inflection such that the depressed first cam-engaging surface 533b contacts the camming switch 532 and the upward bias of the leaf spring 534 on the cammed lever 533 against the camming switch 532 effectively enables the depressed first cam-engaging surface 533b to capture the lower portion of the camming switch 532.

Those of skill in the art will appreciate that the handle 502 may be allowed to be sufficiently open such that the ratchet-toothed member 531 is longitudinally separated from the pawl member 538 and positioning the camming switch 532 at an angle associated with the engaged, released, or defeated states will prepare the handle for a desired state when the handle members 504, 506 are pivoted toward each other.

Those of skill in the art will appreciate that curved exterior surfaces of the handle embodiments of the present invention may provide a distinctive ornamental appearance of the device. The curved surfaces may also provide ergonomic advantages for a user, which could also be provided by curved surfaces having a different ornamental appearance. It is intended that the foregoing detailed description be regarded as illustrative rather than limiting. It should be understood that the following claims, including all equivalents, are intended to define the spirit and scope of this invention.

We claim:
1. An in-line surgical instrument having a handle operatively connected to an elongate shaft, the handle comprising:
 a first handle member;
 a second handle member pivotably connected to the first handle member near a proximal end of both handle members; and
 a ratchet mechanism disposed distal relative to the pivotable connection and configured for removably engaging the first and second handle members, the ratchet mechanism comprising first and second ratchet mechanism portions,
 wherein the first ratchet mechanism portion comprises:
 an L-shaped ratchet-toothed engagement member;
 a cammed lever member; and
 a camming switch;
 wherein the L-shaped ratchet-toothed engagement member is mounted pivotably to and projects from the first handle member toward the second handle member, the L-shaped ratchet-toothed engagement member comprising a toothed portion generally perpendicular to a lever-arm projection portion;
 wherein the camming switch is mounted pivotably to and projects from the first handle member away from the second handle member;
 wherein the cammed lever member comprises a camming end, a levering end, a pivot axis therebetween connecting the cammed lever member pivotably to the first handle member; and
 wherein the camming switch contacts the camming end of the cammed lever member and the levering end of the cammed lever member contacts the lever-arm projection of the L-shaped ratchet-toothed engagement member;
 the camming end comprising a protruding camming surface and a depressed camming surface; and
 wherein the second ratchet mechanism portion comprises:

a pawl member mounted to the second handle member, the pawl member including a pawl tooth portion and a pawl leg portion, wherein the pawl tooth portion projects toward, and is configured to engage with, the toothed portion of the ratchet-toothed engagement member; and wherein, a biasing spring contacting the L-shaped ratchet-toothed engagement member biases said L-shaped ratchet-toothed engagement member into engagement with the pawl tooth portion when the camming switch is oriented at a neutral position between a first angle and a second angle; and wherein, the camming switch and the camming end of the cammed lever member are configured such that when the camming switch is disposed at the first angle relative to the cammed lever member, a first operative contact between the camming switch and the protruding camming surface of the cammed lever member levers the L-shaped ratchet-toothed engagement member out of its biased engagement with the pawl tooth portion of the pawl member; and wherein, the camming switch and the camming end of the cammed lever member are also configured such that when the camming switch is disposed at the second angle relative to the cammed lever member, a second operative contact between the camming switch and the depressed camming surface of the cammed lever member levers the L-shaped ratchet-toothed engagement member out of its biased engagement with the pawl tooth portion of the pawl member.

2. The in-line surgical instrument of claim 1, wherein the second operative contact comprises a frictional engagement simultaneously locking the camming switch at the second angle and the L-shaped ratchet-toothed engagement member out of its biased engagement with the pawl tooth portion of the pawl member.

* * * * *